(12) United States Patent
Ulrich et al.

(10) Patent No.: US 7,173,009 B2
(45) Date of Patent: Feb. 6, 2007

(54) SURFACTANT PROTEIN C ESTERS

(75) Inventors: Wolf-Rüdiger Ulrich, Constance (DE); Ernst Sturm, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 11/287,197

(22) Filed: Nov. 28, 2005

(65) Prior Publication Data

US 2006/0148701 A1    Jul. 6, 2006

Related U.S. Application Data

(63) Continuation of application No. 09/959,628, filed as application No. PCT/EP00/05031 on Jun. 2, 2000, now Pat. No. 7,022,671.

(30) Foreign Application Priority Data

Jun. 17, 1999  (EP)  .................. 99111728

(51) Int. Cl.
*A61K 38/00*  (2006.01)
(52) U.S. Cl. ............................ 514/12; 514/2
(58) Field of Classification Search .............. None
See application file for complete search history.

(56) References Cited

U.S. PATENT DOCUMENTS 5,874,406 A  *  2/1999  Schafer et al. ................ 514/12

5,876,970 A       3/1999  Benson et al.

FOREIGN PATENT DOCUMENTS

| EP | 0 458 167 A1 | 11/1991 |
|---|---|---|
| EP | 0 458 167 B1 | 11/1991 |
| WO | 89/04326 A1 | 5/1989 |
| WO | 91/18015 A1 | 11/1991 |
| WO | 95/32992 A1 | 12/1995 |
| WO | 97/19108 A1 | 5/1997 |

OTHER PUBLICATIONS

Johansson, J., "Structure and properties of surfactant protein C", *Biochimica et Biophysica Acta*, vol. 1408, pp. 161-172, (1998).
Nagasawa, H.T., "Augmentation of Human and Rat Lenticular Glutathione in Vitro by Prodrugs of γ-L-Glutamyl-L-cysteine", *J. Med. Chem.*, vol. 39, pp. 1676-1681, (1996).
Possmayer, F., "Pulmonary Perspective: A Proposed Nomenclature for Pulmonary Surfactant-associated Proteins[1-3]", *Am. Rev. Respir. Dis.*, vol. 138, pp. 990-998, (1988).
"Effects of rSP-C Surfactant on Oxygenation and Histology in a Rat-Lung-Lavage (RLL) Model of Acute Lung Injury", *Am. J. Respir. Crit. Care Med.*, vol. 158, pp. 270-278, 1998.

* cited by examiner

*Primary Examiner*—B. Dell Chism
(74) *Attorney, Agent, or Firm*—Nath & Associates, PLLC; Joshua B. Goldberg; Sheldon M. McGee

(57) ABSTRACT

Novel surfactant protein C esters suitable for preparing pharmaceutical compositions for the treatment of infant respiratory distress syndrome and adult respiratory distress syndrome are described.

4 Claims, 1 Drawing Sheet

SURFACTANT PROTEIN C ESTERS

This application is a continuation application of 09/959,628, filed Nov. 1, 2001, now U.S. Pat. No. 7,022,671, which is a 371 of PCT/EP00/05031, filed Jun. 2, 2000.

TECHNICAL FIELD

The invention relates to pulmonary-surfactant-active polypeptides (surfactant proteins), to processes for their preparation and to pharmaceutical compositions comprising them.

PRIOR ART

The lungs of all vertebrates contain a substance mixture called "pulmonary surfactant". It has surface-active properties and reduces surface tension in the alveolar region of the lungs to such an extent that collapse of the final regions of the respiratory tract during exhaling is avoided. This substance mixture regulates the surface tension dynamically, so that the collapse of the small alveoli, which is to be expected according to Laplace's law, is avoided in favor of the greater ones, by appropriate adjustment of the surface tension. This results in a well-balanced, histologically and physiologically stable structure of the lung.

Pulmonary surfactant is secreted by the alveolar pneumocytes of type II in the form of lamellar bodies. These are compact units of phospholipid bilayers having a high proportion of dipalmitoylphosphatidylcholine (DPPC) and phosphatidylglycerol (PG). As further essential components, the pulmonary surfactant contains proteins designated SP-A, SP-B, SP-C and SP-D (Possmayer, F.: A Proposed Nomenclature for Pulmonary Surfactant-Associated Proteins. Am. Rev. Respir. Dis. 1988, 138, 990–998). SP-A is a high-molecular-weight glycoprotein which plays a decisive role in the regulation of secretion.

During the formation of the monomolecular surface film (in a narrow sense), the proteins SP-C and, to a lesser extent, SP-B play the role of "thermodynamic catalysts". The presence of these proteins accelerates the spreading kinetics enormously. Only because of this, adjustment of the surfactant to the prevailing surface tension requirements is possible without delay. These properties are reflected in the extremely hydrophobic character of the proteins, in particular of SP-C.

By extraction of lung tissue or lavage of animal lungs, it has been possible to obtain surfactant preparations which are capable of compensating for a surfactant deficit both in physicochemical measuring apparatus and in animal models and in clinical use as well, thus being suitable, for example, for the therapy of infant respiratory distress syndrome (IRDS). However, these animal preparations have serious shortcomings:

The phospholipid composition depends strongly on the animal species and on the health and the nutritional condition of the animal, and compensation by admixture of defined components is only possible to a limited extent. The surfactant protein content and the ratio SP-B/SP-C are subject to the same variations. In addition, proteolytic degradation products of the proteins or modified derivatives (for example by oxidation at methionine) may also be present in the mixture which is used therapeutically. In cases of long-term use or the administration of large amounts of surfactant, which could be required, for example, in cases of adult respiratory distress syndrome (shock lung, ARDS) or in other areas of use, for example the use of surfactant to "drag" other substances in pulmonary administration, the question of the supply of the substance remains open.

It would therefore be appropriate to solve these problems by preparing the proteins by genetic engineering. Since recombinant proteins, in particular when bacterial expression systems are used, can be prepared in virtually unlimited amounts, and the use of modern analysis methods and quality controls is possible, a surfactant having an exactly-defined composition can be prepared by using synthetic phospholipids. This surfactant can be adapted optimally to the therapeutic requirements.

The central part of the human protein SP-C, (SEQ ID NO:1, see the formula I below, where A=absent or Phe, B=Cys and C=Met), which is of particular importance for spreading kinetics, consists exclusively of aliphatic, highly hydrophobic amino acids, such as valine, leucine and iso-leucine. The length of this central part (amino acids 12–34 in formula I) allows the integration of the peptide into the monomolecular phospholipid film. The two Cys radicals in the sequence SEQ ID NO:2 Pro-Cys-Cys-Pro (position 3–6 in formula I) are thioesterified at the SH groups by palmitic acid. The palmitic acid increases the hydrophobic character of the entire protein even further and at the same time blocks the two SH groups of the cysteins, protecting them against oxidation and disulfide-bridge formation. The central region (amino acids 13–34 in formula I) forms a transmembrane helix. The N terminus of this region is flanked by a polar sequence containing positively charged amino acids (Lys, 10; Arg, 11 in formula I).

WO89/04326 and WO91/18015 describe the preparation of recombinant SP-C and of mutants of SP-C. In these publications, it is proposed, inter alia, to replace the two cysteins in position 4 and 5 by two serine radicals. In the preparation, this has the advantage that the technically-complicated palmitolation of the two cysteins after the isolation of the highly hydrophobic protein can be dispensed with.

WO95/32992 describes SP-C mutants which differ from human SP-C in that the two cysteins in positions 4 and 5 are replaced by phenylalanine or tryptophan and the methionine in position 32 is replaced by isoleucine, leucine or serine.

U.S. Pat. No. 5,876,970 describes, inter alia, mass spectrometry analysis of surfactant protein C isolated from various natural sources. It is mentioned that, during the work-up of SP-C samples for mass spectrometry, a methyl or isopropyl ester may have been formed.

DESCRIPTION OF THE INVENTION

It is the object of the present invention to provide further surfactant proteins suitable for producing pharmaceutical pulmonary surfactant preparations. Surprisingly, it has now been found that SP-C polypeptides which are esterified at the carboxy terminus with alcohols having 1–4 carbon atoms have, firstly, advantageous properties with respect to their pulmonary surfactant activity and, secondly, advantageous properties with respect to their stability. In particular, the SP-C esters according to the invention have a low tendency to aggregate and accordingly improved stability in solution.

One aspect of the invention therefore relates to SP-C polypeptides in which the amino acid at the carboxy terminus of the polypeptide is esterified with an alcohol having 1–4 carbon atoms, and salts thereof.

In the context of the invention, the term "SP-C" is to be understood, in analogy to the nomenclature proposed by Possmayer (Possmayer, F.: A Proposed Nomenclature for Pulmonary Surfactant-associated Proteins. Am. Rev. Respir.

Dis. 1988, 138, 990–998), as the "family" of surfactant proteins which is present in natural pulmonary surfactant or in the amniotic fluid of mammals and designated SP-C. SP-C is preferably understood as meaning the surfactant protein SP-C which is present in human pulmonary surfactant or in human amniotic fluid.

Furthermore, the term "SP-C" also includes chemically synthesized or recombinantly prepared SP-C and modifications of SP-C, for example those modifications where one or more amino acids are missing or have been replaced by other amino acids. Chemically synthesized or recombinantly prepared SP-C and modifications of SP-C are described, for example, in WO89/04326, WO91/00871, WO91/18015, WO93/21225 and also in WO95/32992.

In a preferred embodiment of the invention, SP-C is understood as meaning a surfactant protein known from WO95/32992 with the amino acid sequence SEQ ID NO:3 of the formula I.

```
  0    1   2    3   4   5    6   7    8   9   10
(A)  Gly Ile Pro   B   B  Pro Val His Leu Lys 11  12  13  14  15  16  17  18  19  20
     Arg Leu Leu Ile Val Val Val Val Val Val  (I), 21  22  23  24  25  26  27  28  29  30
     Leu Ile Val Val Val Ile Val Gly Ala Leu 31  32  33  34
     Leu   C Gly Leu
``` in which A is absent or Phe, B is Phe or Trp and C is Ile, Leu or Ser.

Preference is given to those surfactant proteins of the formula I in which A is absent or Phe, B is Phe and C is Ile. Particular preference is given to a surfactant protein of the formula I in which A is absent, B is Phe and C is Ile [hereinbelow also referred to as SP-C (FF/I) or rSP-C (FF/I)].

The amino acid sequences are shown in the customary short notation (three-letter code) according to the nomenclature, with the amino acid which carries the free amino group at the left end (amino terminus; amino acid of the number 0 or 1 in formula I) and the amino acid which carries the free carboxyl group at the right end (carboxy terminus; amino acid of the number 34 in formula I).

In a mixture with phospholipids, the SP-C esters according to the invention have pulmonary surfactant activity. The pulmonary surfactant activity can be determined in a manner known to the person skilled in the art. Natural pulmonary surfactant has surface-active properties; it reduces, for example, the surface tension in the pulmonary alveoli. A simple and rapid in vitro test for the determination of the surface activity of pulmonary surfactant preparations is, for example, the so called Wilhelmy balance [Goerke, J. Biochim. Biophys. Acta, 344: 241–261 (1974), King R. J. and Clements J. A., Am. J. Physicol. 223: 715–726 (1972)]. This method gives an indication of the pulmonary surfactant quality, measured as the ability of a pulmonary surfactant to reach a surface tension of nearly zero mN/m. Another measuring device to determine the surface activity of pulmonary surfactant is the "pulsating bubble surfactometer" [Possmayer F., Yu S. and Weber M., Prog. Resp. Res., Ed. v. Wichert, Vol. 18: 112–120 (1984)]. The activity of a pulmonary surfactant composition can also be determined by means of in vivo tests. By the measurement of, for example, the pulmonary compliance, the blood gas exchange or the respiratory pressures needed in animal models of ARDS and IRDS, it is possible to obtain an indication of the activity of a pulmonary surfactant. Such a model is described, for example, by Häfner et al. (D. Häfner et al.: Effects of rSP-C surfactant on oxygenation and histology in a rat lung lavage model of acute lung injury. Am. J. Respir. Crit. Care Med. 1998, 158: 270–278).

In the context of the invention, an alcohol having 1–4 carbon atoms is to be understood as meaning, in particular, an aliphatic alcohol having 1–4 carbon atoms. Methanol, ethanol, 1-propanol, 2-propanol (isopropanol), 1-butanol and 2-butanol may be mentioned here, with methanol and 2-propanol being preferred.

Suitable salts for the SP-C esters according to the invention are, in particular, acid addition salts with acids. Particular mention may be made of the pharmacologically acceptable salts of the strong acids customarily used in pharmacy. Suitable are, advantageously, acid addition salts with acids such as, for example, hydrochloric acid, hydrobromic acid and sulfuric acid, where, in the preparation of the salt, the acids are employed in an equimolar ratio or in a ratio differing therefrom—depending on whether it is a mono- or polybasic acid and on which salt is desired.

The SP-C ester can be prepared starting with the corresponding surfactant protein C having the free carboxyl group at the carboxy terminus, by reaction with the appropriate alcohol under suitable esterification conditions. The invention accordingly also provides a process for preparing the SP-C esters according to the invention by reacting the corresponding surfactant protein C having the free carboxyl group at the carboxy terminus with a desired alcohol under suitable esterification conditions. Preference is given to employing a large excess of alcohol as solvent and to carrying out the esterification with the aid of an acid. With respect to the hydrophobic character of the surfactant proteins, it is advantageous to employ the alcohol in a mixture with other organic solvents. These other organic solvents are preferably halogenated hydrocarbons, such as, for example, chloroform and dichloromethane. Suitable acids are, in particular, strong acids, such as, for example, hydrochloric acid, sulfuric acid or hydrobromic acid. To avoid the formation of decomposition products, the esterification is preferably carried out at temperatures at or below room temperature. After the esterification the resulting esters are isolated in a customary manner and, if appropriate, purified, for example by column chromatography with a suitable solvent (for example as described in WO95/32992 or WO92/00993). The isolation or preparation of exemplary surfactant proteins C which can be used as starting materials for the esterification is described, for example, in WO89/04326, WO91/00871, WO91/18015, WO93/21225 or else in WO95/32992. The preparation of rSP-C (FF/I) is described in WO95/32992. It is possible, for example, to process the rSP-C (FF/I) solutions obtained therein after chromatographic purification of the protein (see WO95/32992, page 10, second paragraph) directly into the corresponding rSP-C (FF/I) esters.

The SP-C esters according to the invention can, on their own or in combination with one another, be provided in pharmaceutical compositions which are matched to the requirements of the treatment of the respiratory tract. The combination of the SP-C esters according to the invention with at least one further pulmonary-surfactant-active polypeptide from the group SP-A, unesterified SP-C and SP-B in pharmaceutical compositions may be mentioned. In particular, the combination with unesterified SP-C in pharmaceutical compositions may be mentioned here. Preference is given to combinations which (based on the total amount of surfactant protein in the compositions) comprise up to 50% by weight of SP-C (unesterified), the remainder being one or more SP-C esters according to the invention, or combinations comprising up to 50% by weight of one or more of the SP-C esters according to the invention, the remainder being SP-C (unesterified). Particular preference is given to combinations which comprise 5 to 15% by weight of SP-C (unesterified), the remainder being one or more of the SP-C esters according to the invention, or combinations comprising 0.5 to 10% by weight of one or more of the SP-C esters according to the invention, the remainder being SP-C (unesterified), in particular those comprising 2 to 5% by weight of SP-C esters, the remainder being SP-C (unesterified). Preference is given here to the combination of rSP-C (FF/I) esters and rSP-C (FF/I) in unesterified form. Exemplary combinations comprise 1–6% by weight of rSP-C (FF/I) methyl ester, the remainder being rSP-C (FF/I) in unesterified form. Such combinations can be obtained, for example, directly from the esterification reaction of SP-C if the esterification reaction is interrupted before complete conversion is achieved, or by mixing the appropriate pure components of the combination.

In addition to the surfactant protein, the compositions comprise phospholipids, preferably phospholipids which are contained in natural pulmonary surfactant compositions, such as, preferably, dipalmitoylphosphatidylcholine (DPPC), palmitoyloleylphosphatidylglycerol (POPG) and/or phosphatidylglycerol (PG). Further possible components of the compositions according to the invention are fatty acids, such as, for example, palmitic acid. To adjust the favorable viscosity, the compositions may comprise electrolytes, such as calcium, magnesium and/or sodium salts (for example calcium chloride, sodium chloride and/or sodium bicarbonate). When determining the type and the amounts of the individual components of the compositions, the person skilled in the art uses, on the one hand, the known composition of natural pulmonary surfactants and, on the other hand, the numerous proposals made in the prior art, such as, for example, EP-A 0119056 and EP-A 0406732, for orientation.

Preparations according to the invention expediently comprise 80 to 95% by weight of phospholipids, 0.2 to 5% by weight of surfactant protein, 2 to 15% by weight of fatty acids and 0 to 5% by weight of electrolytes (based on the dry weight).

The phospholipids are preferably mixtures of dipalmitoylphosphatidylcholine (DPPC) and palmitoyloleylphosphatidylglycerol (POPG), in particular in a ratio (ratio by weight) of from 7 to 3 to 3 to 7.

Preferred preparations according to the invention comprise 80 to 95% by weight of phospholipids, 0.5 to 3.0% by weight of surfactant protein, 3 to 15% by weight of fatty acid, preferably palmitic acid, and 0 to 3% by weight of calcium chloride (based on the dry weight).

Preferred compositions according to the invention comprise 80 to 95% by weight of phospholipids, 0.5 to 3.0% by weight of surfactant protein, 4 to 7% by weight of fatty acid, preferably palmitic acid, and 1 to 3% by weight of calcium chloride.

The preparations according to the invention are produced in a manner known to the person skilled in the art, for example by incorporating the surfactant protein into a phospholipid matrix as described in WO95/32992. According to the invention, the pulmonary surfactant preparations are preferably provided in lyophilized and in particular in spray-dried form. Lyophilized preparations are known, for example, from WO97/35882, WO95/32992, WO91/100871 and DE 3229179. WO97/26863 describes a process for preparing pulverulent pulmonary surfactant preparations by spray-drying. According to the invention, preference is given to preparations prepared in this manner.

EXAMPLES 1. rSPC (FF/I) ester rSPC (FF/I) methyl ester

In a separating funnel, 5 fractions (1 l) of the pure rSPC (FF/I) solutions obtained according to WO95/32992 by HPLC chromatography are admixed with 500 ml of chloroform and 300 ml of 1 N hydrochloric acid and mixed thoroughly, and the aqueous phase is then, after phase separation, removed. The organic phase is diluted with methanol to 1 l and washed once more with 300 ml of 1 N hydrochloric acid. After phase separation, the organic phase is again diluted with methanol to 1 l, and the pH of the solution is adjusted to about pH 1 using conc. hydrochloric acid. The mixture is allowed to stand at room temperature for 2 days, and about 300 ml of solvent mixture are then distilled off using a rotary evaporator. After a further 3 days at room temperature, it is no longer possible to detect unesterified rSPC (FF/I) by HPTLC (ready-to-use HPTLC plates Diol (Merck); mobile phase; chloroform:methanol: ammonia (25%):$H_2O$=13:6:0.4:0.8; staining: Comassie Blue). The solution is extracted twice with in each case 300 ml of 0.1 N hydrochloric acid and the organic phase is, after phase separation, diluted in each case with 2-propanol to about 700 ml. The pH of the solution is adjusted with saturated $NaHC_3$ solution to pH 3.5–4. Altogether 4×, the solution is concentrated at 20–25° C. to 250 ml using a rotary evaporator and in each case made up to 500 ml using 2-propanol. Filtration finally gives a solution of about 200 mg of rSPC (FF/I) methyl ester in 2-propanol which is stored at −20° C. The mass spectrum (MALDI-TOF) shows the molecule peak $MH^+$ at 3634 Da.

rSPC (FF/I)-2-propyl ester

In a separating funnel, 6 fractions (1.2 l) of the pure rSPC (FF/I) solutions obtained according to WO95/32992 by HPLC chromatography are admixed with 500 ml of chloroform and 400 ml of 1 N hydrochloric acid and mixed thoroughly, and the aqueous phase is, after phase separation, removed. The organic phase is diluted with 2-propanol to 1.2 l, and the pH is then adjusted to 0.5–1 using conc. hydrochloric acid. The mixture is allowed to stand at room temperature for 1 day, and about 300 ml of solvent mixture are then distilled off at 20–25° C. using a rotary evaporator and replaced by 300 ml of 2-propanol. This procedure is repeated after 3, 6, 9 and 12 days of standing at room temperature. By HPTLC (see Example 1), it is then virtually impossible to detect any unesterified rSPC (FF/I). The pH of the solution is adjusted to 3.5–4 using sat. $NaHCO_3$ solution, and the solution is then concentrated to 500 ml using a rotary evaporator. Filtration gives a solution of about 250 mg of rSPC (FF/I) 2-propyl ester in 2-propanol which is stored at −20° C. The mass spectrum (MALDI-TOF) shows the molecule peak $MH^+$ at 3662 Da.

2. Incorporation of rSP-C (FF/I) esters into a Phospholipid Matrix rSP-C (FF/I) methyl or 2-propyl ester in a solution of isopropanol is admixed with the components of the phospholipid matrix and, by spraying into a dilute sodium chloride solution (0.065% w/w NaCl) at room temperature precipitated as a homogeneous mixture with the components of the phospholipid matrix. From the pulmonary surfactant suspension, the pulmonary surfactant (LSF) is separated off using a bucket centrifuge and resuspended in electrolyte solution (NaCl, CaCl$_2$), and the pH is adjusted to pH 6.5 using 0.1N NaOH. This aqueous suspension is filled into 20 ml vials and lyophilized. The weights and volumes stated in the preparation example below are based on the preparation of 10 g of pulmonary surfactant preparation:

At 40° C., 7.00 g of dipalmitoylphosphatidylchloline (DPCC), 3.08 g of palmitoyloleylphosphatidylglycerol ammonium salt (POPG×NH$_4$) and 0.25 g of palmitic acid are dissolved in 200 ml of 90% isopropanol, and the mixture is then cooled to room temperature. The resulting phospholipid solution is combined with 1 l of a solution comprising 200 mg of SP-C (FF/I) methyl or 2-propyl ester. The resulting "spray solution" is adjusted to pH 4.5 by stirring with bicarbonate solution (about 5 ml of 5% NaHCO$_3$ solution).

At room temperature, the "spray solution" is introduced with vigorous stirring via a single-substance nozzle at a spray rate of 25 m/min into 9.6 l of dilute NaCl solution (0.065% w/w). An opalescent solution forms from which, after 2 hours of storage at 4° C.–8° C., the pulmonary-surfactant preparation is precipitated by spraying in an electrolyte solution (3.0 g CaCl$_2$×2H$_2$0 and 61.3 g NaCl in 300 ml H$_2$O). The pulmonary surfactant suspension (total volume 10.8–11.01 l) is stored at 4C. over night and then centrifuged for in each case 30-minutes using a Sorvall bucket centrifuge (RC2-B) at 16,000 g. In each case, the centrifugation cake is, to remove adhering remaining isopropanol, resuspended in half of its volume of 0.65% strength sodium chloride solution and centrifuged again. This procedure is repeated for a total of 3–4 times. The cake of the last centrifugation is taken up in 400 ml of 0.65% strength NaCl solution, adjusted to pH 6.5 using 0.1 N NaOH and divided, in portions of 6.2 g, into 20 ml vials. The content of the vials is lyophilized as follows: freezing at −45° C. and atmospheric pressure for 6 hours, freeze-drying at 0.16 mbar and −20° C. for 54 hours and then, for further intensive drying, another 5 hours at −20° C. and 0.02 mbar.

This gives 65–66 vials each containing 0.150 g of pulmonary surfactant (calc. without NaCl).

The dry pulmonary surfactant samples are stored in a fridge at 4° C. and have to be resuspended with water or physiological saline prior to use (concentration of the suspension 25 mg/ml).

Each vial contains:

| | |
|---|---|
| 95.6 mg | of dipalmitoylphosphatidylcholine |
| 42.1 mg | of palmitoyloleylphosphatidylglycerol (ammonium salt) |
| 2.7 mg | of rSP-C(FF/I) methyl or 2-propyl ester |
| 6.8 mg | of palmitic acid |
| 2.9 mg | of calcium chloride (anhydrous) |

3. Production of Pulverulent Pulmonary Surfactant Preparations

Pulverulent-pulmonary surfactant preparations are produced by the process described in WO97/26863.

Example A

At 50° C., 10.95 g of 1,2-dipalmitoyl-3-sn-phosphatidylcholine, 4.6 g of 1-palmitoyl-2-oleoyl-3sn-phosphatidylglycerol-ammonium, 418 mg of calcium chloride dihydrate and 750 mg of palmitic acid are dissolved in 330 ml of 2-propanol/water (85:15) and, after cooling to 30° C., mixed with 620 ml of a solution of rSP-C (FF/I) 2-propyl ester in isopropanol/water (95:5, c=484 mg/l). The resulting solution is spray-dried in a Büchi B 191 laboratory spray dryer. Spraying conditions: gas for drying: nitrogen, inlet temperature: 100° C., outlet temperature: 58–60° C. This gives a colorless powder.

Example B

At 50° C., 3.74 g (5.1 mmol) of 1,2-dipalmitoyl-3-sn-phosphatidylcholine, 2.81 g (3.7 mmol) of 1-palmitoyl-2-oleoyl-3-sn-phosphatidylcholine, 2.90 g (3.9 mmol) of 1,2-dipalmitoylphosphatidyl-3-sn-phosphatidylglycerol sodium, 234 mg of palmitic acid and 279 mg (1.9 mmol) of calcium chloride dihydrate are dissolved in 160 ml of 2-propyl ester (65:15) and, after cooling to 30° C. with 566 ml of a solution of rSP-C (FF/I) methyl ester in isopropanol/water (92:8, c=330 mg/l). The resulting solution is spray-dried in a Büchi B 191 laboratory spray dryer. Spraying conditions: gas for drying: nitrogen, inlet temperature: 90° C., outlet temperature: 58–60° C. This gives a colorless powder.

Commercial Utility

Adult respiratory distress syndrome (ARDS) is a descriptive expression which is applied to a large number of acute, diffusely infiltrative pulmonary lesions of different etiology if they are associated with a severe gas exchange disorder (in particular arterial hypoxemia). The expression ARDS is used because of the numerous common clinical and pathological features with the infant respiratory distress syndrome (IRDS). If, in the case of IRDS, the pulmonary surfactant deficiency caused by premature birth is predominant, then in the case of ARDS a pulmonary surfactant malfunction is caused by a lung disorder based on differing etiologies. Triggering causes for an ALI (acute lung injury) including ARDS can, for example, be (cited in accordance with Harrison's Principles of Internal Medicine 10th Ed. 1983 McGraw-Hill Int. Book Comp.) diffuse pulmonary infections (for example due to viruses, bacteria, fungi), aspiration of, for example, gastric juice or in the case of near-drowning, inhalation of toxins or irritants (for example chlorine gas, nitrogen oxides, smoke), direct or indirect trauma (for example multiple fractures or pulmonary contusion), systemic reactions to inflammations outside the lung (for example hemorrhagic pancreatitis, gram-negative septicemia), transfusions of high blood volumes or alternatively after cardiopulmonary bypass.

The compositions according to the invention are not only suitable for the treatment or prophylaxis of IRDS in prematurely born babies or the treatment or prophylaxis of ALI including ARDS in adults, but also for the treatment or prophylaxis of pneumonia, bronchitis, meconium aspiration syndrome, COPD (chronic obstructive pulmonary disease), asthma and cystic fibrosis. Moreover, the surfactant proteins according to the invention and the compositions according to the invention are suitable for use as carriers for the administration of other drugs.

The administration of the compositions according to the invention is carried out in a manner known to the person skilled in the art, preferably by intratracheal instillation (infusion or bolus) or in the form of an atomization. For administration, the compositions according to the invention are preferably dissolved or suspended in a suitable solvent or resuspension medium, in particular when the compositions are present in lyophilized or spray-dried form. The suitable resuspension medium is preferably physiological saline. It has been found to be advantageous to administer suspensions or solutions of the compositions according to the invention containing from 12.5 to 100 mg of phospholipids per ml of suspension. Per application, the compositions according to the invention are preferably administered in such an amount that the amount of phospholipids is between 12.5 and 200 mg per kilogram of body weight. Administration is generally carried out once to three times a day over a period of from 1 to 7 days. If desired, a bronchoalveolar lavage, preferably with dilute pulmonary surfactant composition, can be carried out prior to the administration of the compositions according to the invention. Such a procedure is described, for example, in Gommers et al. [Bronchoalveolar lavage with a diluted surfactant suspension prior to surfactant instillation improves the effectiveness of a surfactant therapy in experimental acute respiratory distress syndrome (ARDS), Intensive Care Med. 1998, 24:494–500] and in WO98/49191.

Accordingly, the invention also provides a method for the treatment or prophylaxis of pneumonia, bronchitis, meconium aspiration syndrome, COPD, asthma, cystic fibrosis, IRDS and/or ALI (including ARDS) in mammals, in particular humans, by administration of a suitable amount of a pulmonary surfactant composition according to the invention.

The invention furthermore provides the use of the surfactant proteins according to the invention for preparing pharmaceutical compositions (medicaments) for the treatment or prophylaxis of pneumonia, bronchitis, meconium aspiration syndrome, COPD, asthma, cystic fibrosis, IRDS and/or ALI (including ARDS) in mammals, in particular humans.

The invention furthermore provides a commercial product, consisting of a customary secondary pack, a primary pack containing the pharmaceutical composition (for example an ampoule) and, if desired, an accompanying leaflet, the pharmaceutical preparation being suitable for the treatment or prophylaxis of pneumonia, bronchitis, meconium aspiration syndrome, COPD, asthma, cystic fibrosis, IRDS and/or ALI (including ARDS), the suitability of the pharmaceutical composition for the prophylaxis or treatment of the disorders mentioned being indicated on the secondary pack or the accompanying leaflet of the commercial product, and the pharmaceutical composition comprising at least one SP-C ester according to the invention, together with suitable pharmaceutical auxiliaries. The secondary pack, the primary pack containing the pharmaceutical composition and the accompanying leaflet otherwise correspond to what the person skilled in the art would consider to be standard for pharmaceutical compositions of this type.

Pharmacological Studies

A composition according to the invention containing rSP-C (FF/I) methyl ester (hereinbelow referred to as batch LLÜ139) and a composition according to the invention containing a combination of rSP-C (FF/I) methyl ester and rSP-C (FF/I) (unesterified) in a ratio by weight (based on the total amount of surfactant protein in the composition) of 5 to 95 (hereinbelow referred to as batch ERa8) were tested in a model described by Häfner et al. [D. Häfner, P.-G. Germann and D. Hauschke: Effects of rSP-C surfactant on oxygenation and histology in a rat-lung-lavage model of acute lung injury. Am. J. Resp. Crit Care Med. 158, 270–278 (1998)]. In the RLL model, the two batches were used by late treatment (administration 1 h after the last lavage) in the dosages 12.5, 25, 50 and 100 mg of phospholipid per kg of body weight. Both batches show a marked improvement of oxygenation compared to untreated controls. The effects are dose-dependent. Specifically, the values at dosages of 50 and 100 mg of phospholipid per kg of body weight are in the range of the initial values of rats which had not been subjected to lavage.

SEQUENCE LISTING

Figure 1:
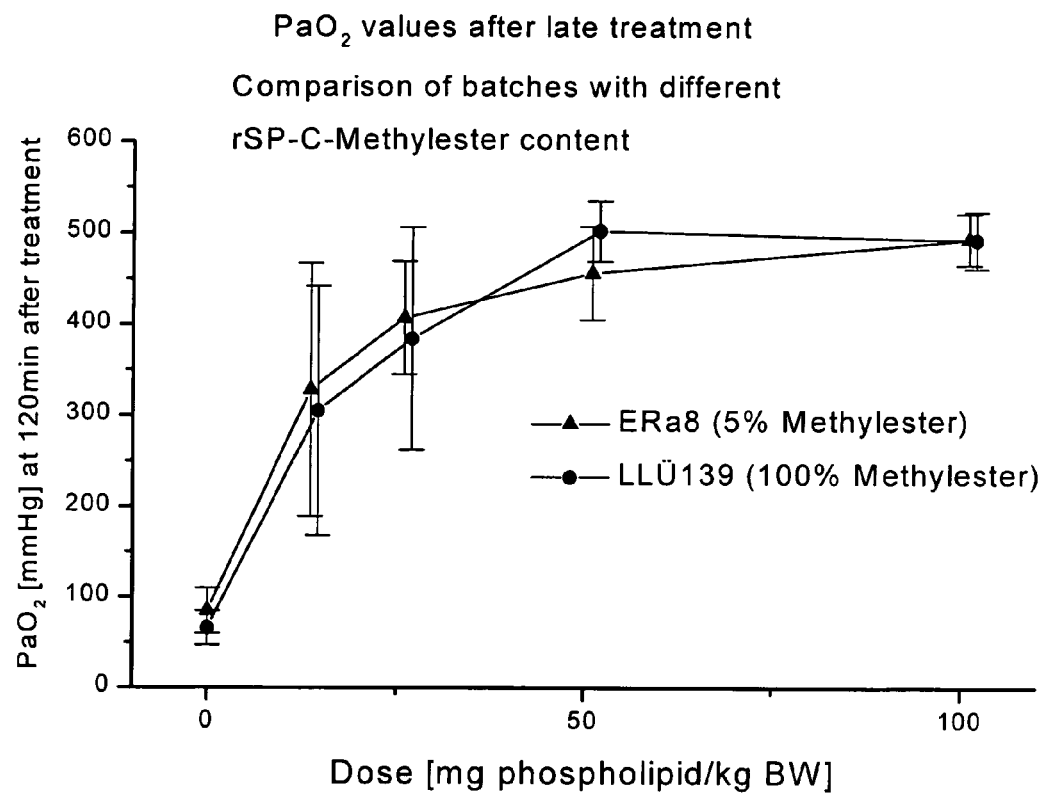
FIG. 1 shows a graphic presentation of the effect of a composition according to the invention containing rSP-C (FF/I), methyl ester (LLÜ139) and a composition according to the invention containing a combination of rSP-C (FF/I) methyl ester and rSP-C (FF/I) (unesterified) in a ratio by weight of 5 to 95 (Era8) for dosages of 12.5, 25, 50 and 100 mg of phospholipid per kg of body weight on the oxygenation in a model described by Häfner et al. [D. Häfner, P.-G. Germann and D. Hauschke: Effects of rSP-C surfactant on oxygenation and histology in a rat-lung-lavage model of acute lung injury. Am. J. Resp. Crit Care Med. 158, 270–278 (1998)]. The dose of 0 mg of phospholipid per kg of body weight represents the oxygenation of untreated controls.

```
<160> NUMBER OF SEQ ID NOS: 3

<210> SEQ ID NO 1
<211> LENGTH: 35
<212> TYPE: PRT
<213> ORGANISM: Homo sapiens
<220> FEATURE:
<221> NAME/KEY: VARIANT
<222> LOCATION: (1)
<223> OTHER INFORMATION: Xaa is Phe or not an amino acid

<400> SEQUENCE: 1

Xaa Gly Ile Pro Cys Cys Pro Val His Leu Lys Arg Leu Leu Ile Val
 1               5                  10                  15

Val Val Val Val Val Leu Ile Val Val Val Ile Val Gly Ala Leu Leu
             20                  25                  30
```

```
-continued
Met Gly Leu
        35

<210> SEQ ID NO 2
<211> LENGTH: 4
<212> TYPE: PRT
<213> ORGANISM: Homo sapiens
<220> FEATURE:
<221> NAME/KEY: NON_TER
<222> LOCATION: (1)
<220> FEATURE:
<221> NAME/KEY: NON_TER
<222> LOCATION: (4)

<400> SEQUENCE: 2

Pro Cys Cys Pro
  1

<210> SEQ ID NO 3
<211> LENGTH: 35
<212> TYPE: PRT
<213> ORGANISM: Homo sapiens
<220> FEATURE:
<221> NAME/KEY: VARIANT
<222> LOCATION: (1)
<223> OTHER INFORMATION: Xaa is Phe or not an amino acid
<220> FEATURE:
<221> NAME/KEY: MUTAGEN
<222> LOCATION: (5)
<223> OTHER INFORMATION: Xaa is Phe or Trp
<220> FEATURE:
<221> NAME/KEY: MUTAGEN
<222> LOCATION: (6)
<223> OTHER INFORMATION: Xaa is Phe or Trp
<220> FEATURE:
<221> NAME/KEY: MUTAGEN
<222> LOCATION: (33)
<223> OTHER INFORMATION: Xaa is Ile, Leu or Ser

<400> SEQUENCE: 3

Xaa Gly Ile Pro Xaa Xaa Pro Val His Leu Lys Arg Leu Leu Ile Val
  1               5                  10                  15

Val Val Val Val Val Leu Ile Val Val Ile Val Gly Ala Leu Leu
             20                  25                  30

Xaa Gly Leu
        35
```

What is claimed is:

1. A method of treating a disorder selected from the group consisting of pneumonia, bronchitis, meconim aspiration syndrome, cystic fibrosis, Infant Respiratory Distress Syndrome (IRDS) and Adult Respiratory Distress Syndrome (ARDS) in a patient, comprising administering to a patient in need thereof a therapeutically effective amount of a surfactant protein C (SP-C) having the amino acid sequence SEQ ID NO: 3 of the formula I

```
      0    1   2   3   4   5   6   7   8   9   10
     (A)  Gly Ile Pro  B   B  Pro Val His Leu Lys 11  12  13  14  15  16  17  18  19  20
          Arg Leu Leu Ile Val Val Val Val Val Val  (I), 21  22  23  24  25  26  27  28  29  30
          Leu Ile Val Val Val Ile Val Gly Ala Leu 31  32  33  34
          Leu     C  Gly Leu
``` in which A is absent or Phe, B is Phe or Trp and C is Ile, Leu or Ser,
wherein the amino acid at the carboxy terminus of the surfactant protein is esterified with an alcohol having 1–4 carbon atoms, and
wherein the esterified surfactant protein C is isolated and purified,
or a pharmacologically acceptable salt thereof.

2. The method according to claim 1, wherein the alcohol is methanol or 2-propanol.

3. The method according to claim 1, wherein A is absent or Phe, B is Phe and C is Ile.

4. The method according to claim 1, wherein A is absent, B is Phe and C is Ile.

* * * * *